(12) United States Patent
Goto et al.

(10) Patent No.: US 8,790,390 B2
(45) Date of Patent: Jul. 29, 2014

(54) ENDOSCOPE TREATMENT TOOL

(75) Inventors: Hiroaki Goto, Tokyo (JP); Ken Fujisaki, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 825 days.

(21) Appl. No.: 12/146,890

(22) Filed: Jun. 26, 2008

(65) Prior Publication Data

US 2009/0005855 A1    Jan. 1, 2009

(30) Foreign Application Priority Data

Jun. 29, 2007    (JP) ................................ P2007-171849

(51) Int. Cl.
*A61F 2/06*    (2013.01)

(52) U.S. Cl.
USPC ........ 623/1.36; 623/1.11; 623/1.15; 623/1.14

(58) Field of Classification Search
USPC .................. 623/1.11, 1.15; 24/453, 455–571; 606/151, 219
See application file for complete search history.

(56) References Cited

U.S. PATENT DOCUMENTS

| | | | | |
|---|---|---|---|---|
| 5,769,887 | A * | 6/1998 | Brown et al. ................. | 623/1.23 |
| 6,350,277 | B1 * | 2/2002 | Kocur .......................... | 623/1.11 |
| 2002/0120277 | A1 | 8/2002 | Hauschild et al. | |
| 2002/0143387 | A1 | 10/2002 | Soetikno et al. | |
| 2003/0220683 | A1 * | 11/2003 | Minasian et al. ............. | 623/1.15 |
| 2005/0102024 | A1 * | 5/2005 | Riccotta et al. .............. | 623/1.23 |
| 2005/0159803 | A1 * | 7/2005 | Lad et al. ...................... | 623/1.13 |
| 2006/0161172 | A1 * | 7/2006 | Levine et al. ................. | 606/108 |
| 2006/0293759 | A1 * | 12/2006 | Berg et al. .................... | 623/23.7 |

FOREIGN PATENT DOCUMENTS

| | | |
|---|---|---|
| EP | 0 554 579 A1 | 8/1993 |
| EP | 0 829 242 A1 | 3/1998 |
| JP | H05-300945 | 11/1993 |
| JP | H06-343703 | 12/1994 |
| JP | 8-502428 | 3/1996 |
| WO | WO 94/12136 | 6/1994 |
| WO | WO 2005/079705 A1 | 9/2005 |

OTHER PUBLICATIONS

Japanese Office Action dated May 8, 2012 issued in counterpart Japanese Patent Application No. 2007-171849.

* cited by examiner

*Primary Examiner* — David Isabella
*Assistant Examiner* — Jacqueline Woznicki
(74) *Attorney, Agent, or Firm* — Scully, Scott, Murphy & Presser, P.C.

(57) ABSTRACT

A stent system 1 has a stent 2 having a hole and at least an anchor 3 having an arm 33. The stent 2 has a cylindrical shape, in which a sheet is rolled, and a plurality of holes 13 are provided thereon. A grasping portion 33A at the distal end of the arm 33 of the anchor 3 can be inserted into the holes 13. A grasping force X of the grip 3 is greater than a drag R that the holes of the stent 2 yield. The grip 3 deforms the stent 2, easily grasps the stent 2 and a biological tissue, whereby it is possible to fix the stent 2. In accordance with the present invention, it is possible to reliably fix the stent in a hollow organ.

4 Claims, 22 Drawing Sheets

ENDOSCOPE TREATMENT TOOL

BACKGROUND OF THE INVENTION

1. Field of the Invention

The present invention relates to an endoscope treatment tool that is used with an endoscope.

Priority is claimed on Japanese Patent Application No. 2007-1718497 filed on Jun. 29, 2007, the content of which is incorporated herein by reference.

2. Description of the Related Art

A stenosis is formed in a hollow organ of a living body and that sometimes makes it impossible for contents to pass therethrough. In such a case, a stent is inserted into the narrowed portion and a procedure is performed to make it open.

For example, if the stenosis is formed in an esophagus, a patient cannot eat, and the quality of life (QOL) of the patient is lowered dramatically.

When the stent is placed in the narrowed portion and the narrowed portion is opened, the patient is able to eat again. For example, in the stent disclosed in Patent Document 1, it is disclosed that the stent made of a twisted wire is placed in the narrowed portion and the narrowed portion is opened.

As a prevention against dislocation of the stent which has been placed, the locking the stent and a clip, which is grasping the hollow organ, by a thread is performed. For example, in the stent disclosed in Patent Document 2, an end portion of the stent and a clip, which is grasped to a surface of the hollow organ separated from the stent, are connected to prevent the dislocation.

Patent Document 1: Japanese Unexamined Patent Application, First Publication No. H06-343703

Patent Document 2: Japanese Unexamined Patent Application, First Publication No. H05-300945

SUMMARY OF THE INVENTION

A first aspect in accordance with the present invention is a stent system having a substantially cylindrical stent and an anchor provided with an arm, in which the stent has at least one hole, the anchor has at least two of said arm provided with distal ends and grasping portions located in the distal ends of the arms. The grasping portion of the arm of at least one of a pair of the arms is inserted in the hole, and the size of the hole, to which the grasping portion is inserted, is at least the size in which a part of the grasping portion can be inserted. X>R is formed when a grasping force of at least the pair of the grasping portion of the arm is X and the force the hole of the stent intending to remain its shape is R.

A second aspect in accordance with the present invention is a stent system having a substantially cylindrical stent and an anchor provided with an arm, in which the stent has at least one hole. The anchor has at least two of said arms provided with distal ends and grasping portions located in the distal ends of the arms, and the grasping portion can be inserted in the hole of the stent The area of the hole is two thirds of an area of a circle having as a diameter the maximum outer diameter of the grasping portion of the anchor.

DETAILED DESCRIPTION OF THE INVENTION

Hereinbelow, embodiments of the present invention shall be described in detail with reference to drawings. Note that in the descriptions of each embodiment, the same reference numbers shall be given to identical portions. Also, descriptions of overlapping portions shall be omitted. As an anchor, a clip for digestive canals (hereinbelow simply called a clip) is used.

(First Embodiment)

Figure 1:
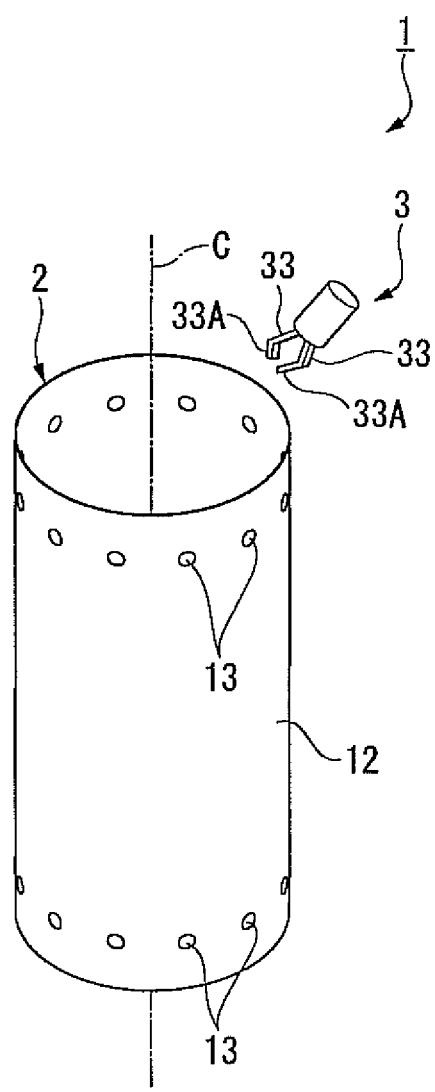
FIG. 1 shows an overview of a stent system in accordance with an embodiment of the present invention.

An overview of a stent system in accordance with the present embodiment is shown in FIG. 1. A stent system 1 has a stent 2 and at least a clip 3 as an anchor which fixes the stent 2.

The stent 2 has a stent main body 12 made of a substantially cylindrical resin film, in which at least one hole 13, which is a locking portion, is formed at both end portions of the stent main body 12. The hole 13 may be disposed at one of the end portions thereof. The stent main body 12 resists a force against deformation which is named R. The hole 13 is formed as a circle when viewed from the lateral direction which is perpendicular to the center axis C of the stent main body 12. The area of the hole 13 is named S. Here, the hole 13 may be an ellipse or another shape.

Figure 2:
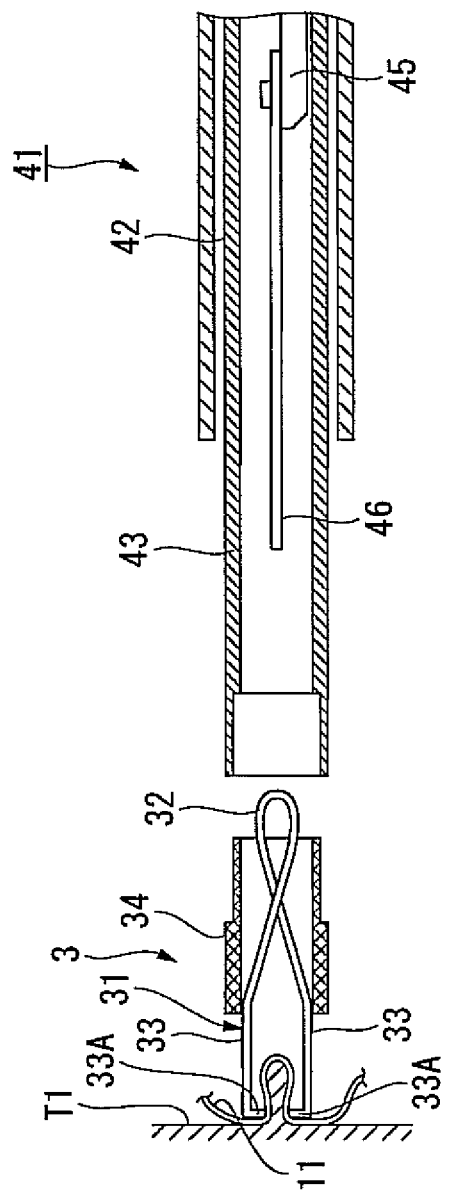
FIG. 2 shows a stent and a biological tissue being grasped by a clip.

As shown in FIG. 1 and FIG. 2, the clip 3 is folded back at the center thereof in a substantially U-shape and then the ends of the clip 3 cross each other to form a ring portion 32 which is a loop shape. In a pair of arms 33, which corresponds to both ends portions of a metal thin plate 31, grasping portions 33A provided at distal ends thereof are bent such that they are closer to each other. The clip 3 is biased so that the pair of grasping portion 33A opens at natural state. By moving a pressing tube 34 so as to pass the crossing point of the ring portion 32 and biasing the side of the distal end of the clip 3 so as to push thereon, the pair of grasping portion 33A closes so as to grasp a biological tissue T1 of an esophagus.

Figure 3:
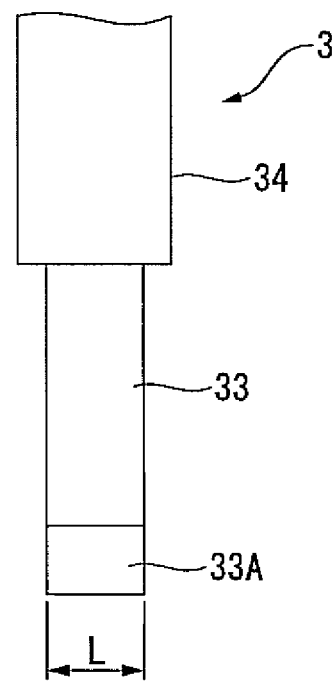
FIG. 3 shows an enlarged view of the grasping portion of a clip.
Figure 4:
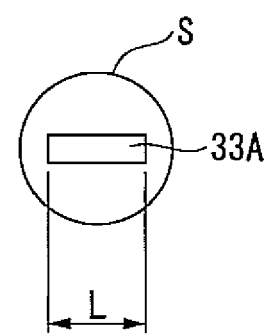
FIG. 4 shows the sizes of the grasping portion and the hole.
Figure 5:
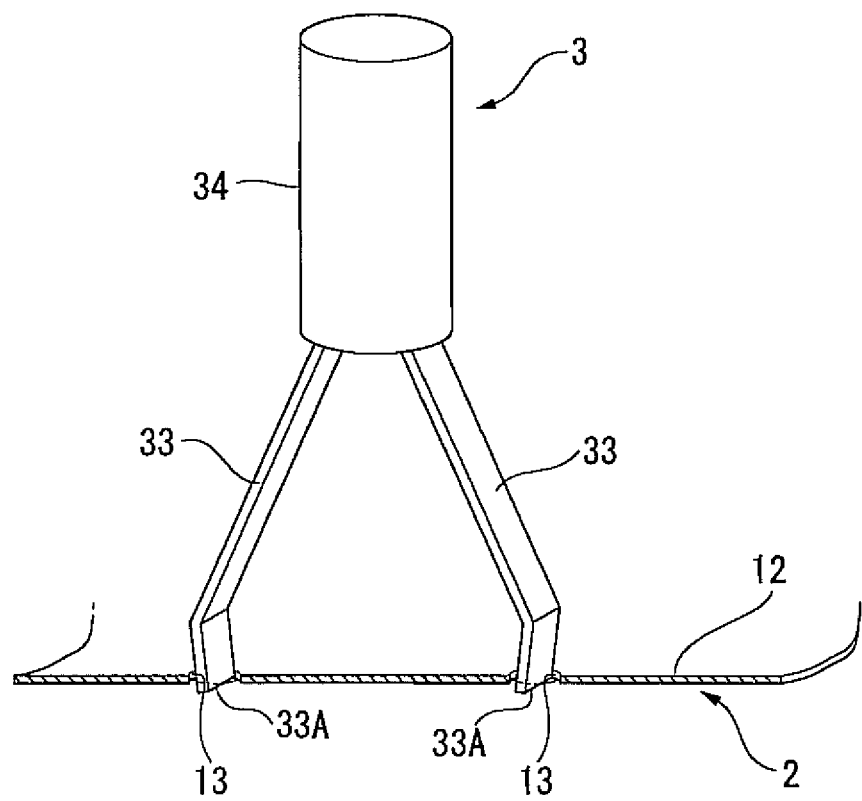
FIG. 5 shows a grasping portion of a clip being passed through the hole.

Here, as shown in FIG. 3, the grasping portion 33A has an elongated shape to be able to be inserted in the hole 13 of the stent 2. The maximum width of the grasping portion 33A is named L. As shown in FIG. 4, the grasping portion 33A is formed so that an area of an imaginary circle, provided with the maximum width L as a diameter, is less than or equal to the area S of the hole 13 of the stent 3. As shown in FIG. 5, the distance between the pair of grasping portions 33A, when the arm 33 is open, is more than or substantially equal to the distance between the two adjacent holes 13 of the stent 2 When the grasping force of the clip is named X, the grasping force X is more than a drag R of the hole 13 of the stent 2.

Figure 6:
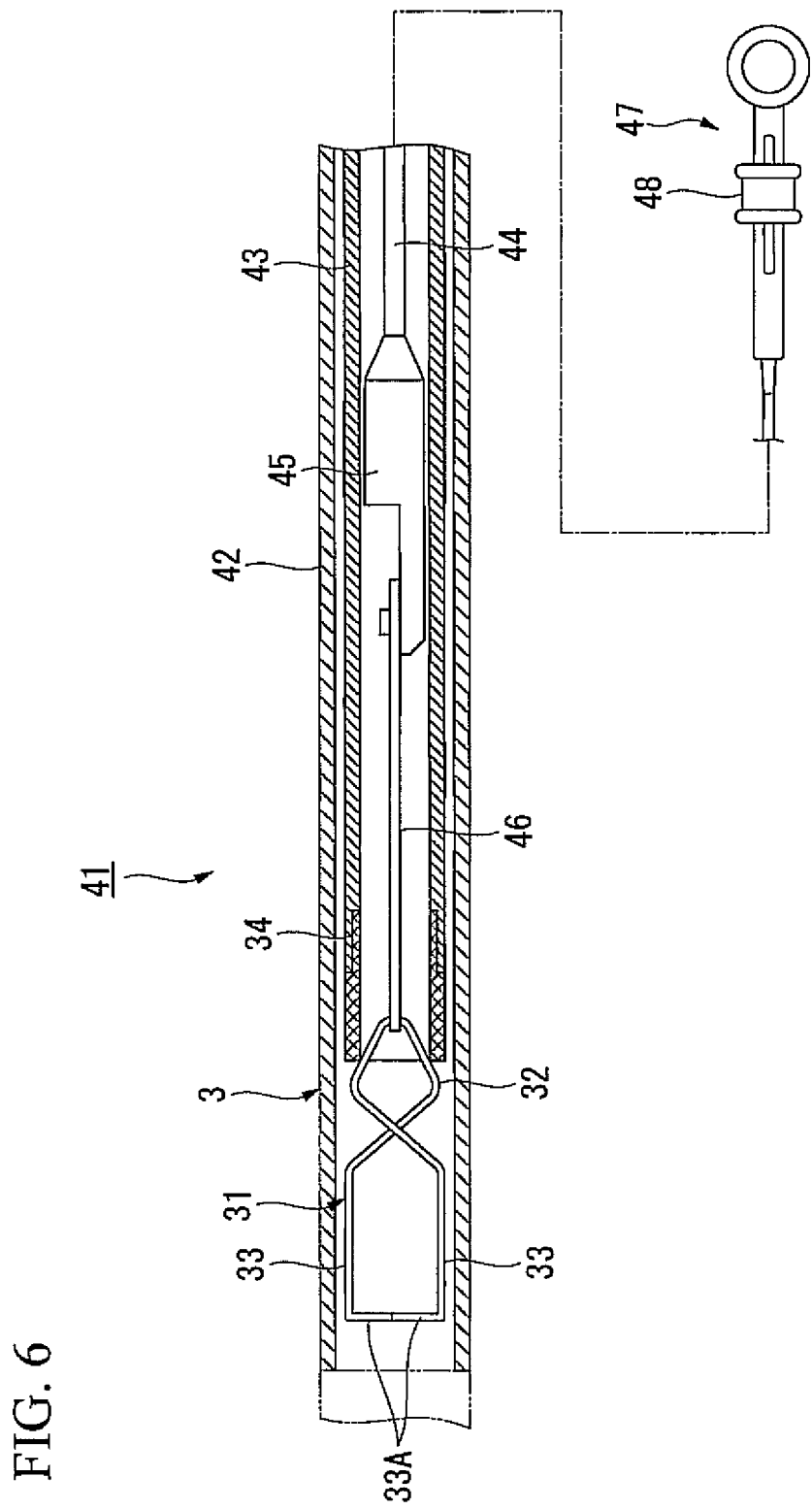
FIG. 6 shows a constitution of a treatment tool which drives a clip with an enlarged cross-section of a distal end portion.

As a device for driving the slip 3 into the biological tissue T1, an instrument tool 41 as shown in FIG. 6 is disclosed. The instrument tool 41 has an outer sheath 42 which is flexible and elongated. A pusher sheath 43 is inserted in the outer sheath 42 so as to freely extend and retract. A pushing tube 34 is connected to the distal end of the pusher sheath 43. Furthermore, in the pusher sheath 43, an operation wire 44 is inserted and a hook 46 is connected via a connection member 45 to the distal end of the operation wire 44. The operation wire 44 is connected to a slider 48 of an operation portion 47 at the proximal side and so it is possible to operate the operation wire 44 extendably and retractably by the slider 48. The hook 46 is hooked in the ring portion 32 of the clip 3. The clip 3 is retracted in the outer sheath 42 and housed therein in a closed state. Inner diameters of the pressing tube 34 and the pusher sheath 43 are smaller than the width of the ring portion 32 at this moment.

Next, an operation of the stent system 1 shall be described.

Figure 7:
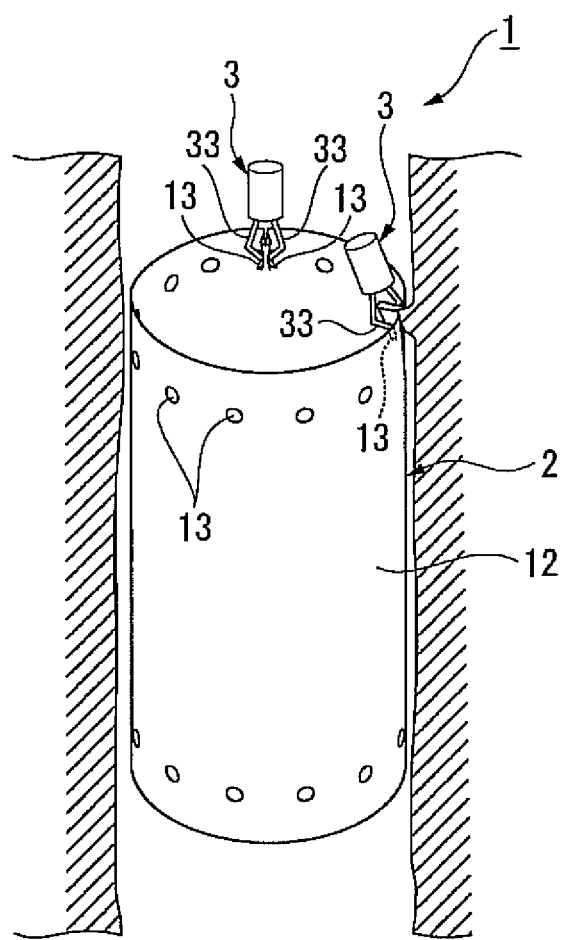
FIG. 7 shows the stent of the present invention being held in place by a clip.

The stent 2 is introduced into a narrowed portion of the esophagus, the clip 3 is driven by using the instrument tool 41. The biological tissue T1 and the stent 2 are grasped. As shown in FIG. 7, the grasping portions 33A of the pair of arms 33 are inserted into the holes 13 and positioning is performed by adjusting the orientation of the grasping portion 33A. The pair of grasping portions 33A may be inserted into the holes 13 one by one or one of the grasping portions 33A may be inserted into the hole 13 and the other of the grasping portions 33A may grasp the biological tissue T1 without inserting into the hole 13.

Figure 8:
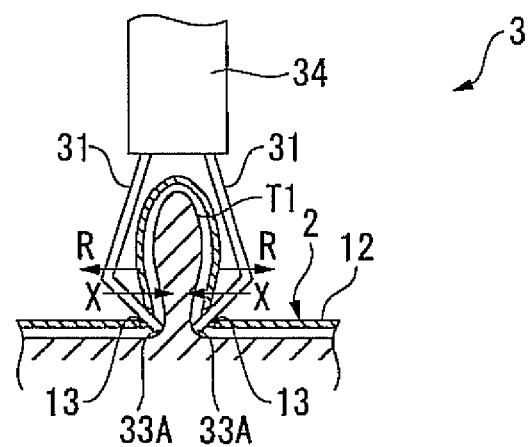
FIG. 8 is an enlarged view of a clip grasping a biological tissue and the stent of the present invention.
Figure 9:
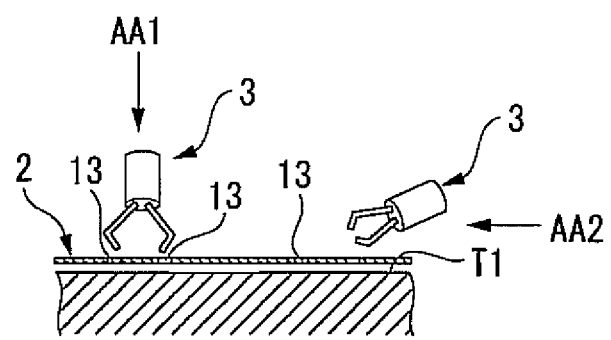
FIG. 9 shows a direction the clip approaches the stent.
Figure 10:
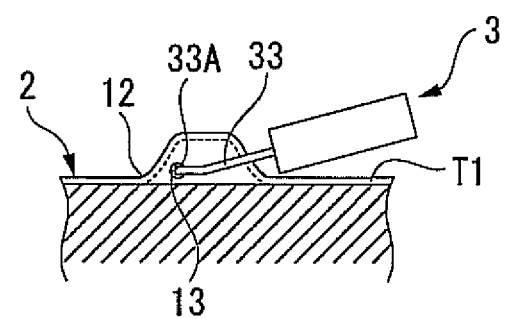
FIG. 10 shows a biological tissue being grasped from a direction shown by the arrow AA2 in FIG. 9.

As shown in FIG. 8, the distance between the grasping portions 33A, when the clip 3 is driven, is shorter than the distance between the holes 13 of the stent 3. Since the grasping force X of the clip 3 is greater than the drag R of the stent 2, a portion of the stent 2 between the holes 13 deforms. Due to this, the stent 2 is fixed to the biological tissue T1 via the clip 3. In FIG. 7, two clips 3 are used but the number of clip 3 may be one or three or more. Here, as shown by the arrow AA1 in FIG. 9, when the clip 3 approaches the circumferential surface of the stent 2 substantially vertically, the stent 3 and the biological tissue T1 are grasped between the pair of arms 33 as shown in FIG. 8. In contrast, as shown by the arrow AM in FIG. 9, when the clip 3 approaches the circumferential surface of the stent 2 substantially in parallel, the stent 3 and the biological tissue T1 are grasped between the pair of arms 33 as shown in FIG. 10.

In the present embodiment, since the holes 13 are provided in the stent 2 and the clip 3 is used for fixing the stent to the biological tissue T1, the stent 2 does not easily dislocate relative to the biological tissue T1. Since the holes 13 are made greater than the grasping portions 33A, it is easy to adjust the orientation of the grasping portion 33A when the grasping portions 33A are inserted in the holes 13. Since the grasping force X of the clip 3 is greater than the drag R when the stent 2 is deformed, it is possible to fix the clip 3 by completely grasping the stent 2 with the clip 3.

Figure 11:
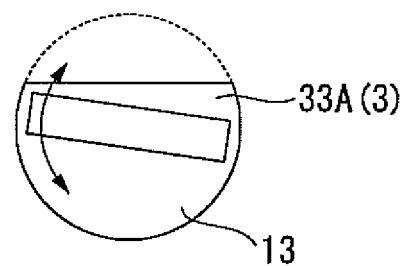
FIG. 11 shows the sizes of the grasping portion and the hole.
Figure 12:
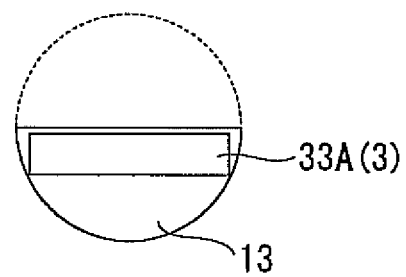
FIG. 12 shows the sizes of the grasping portion and the hole.

Here, the area S of the hole 13 may be two thirds or more of an area D of an imaginary circle provided with the maximum width L of the grasping portion 33A as a diameter. As shown in FIG. 11, it is possible to ensure a degree of freedom in the orientation of the clip 3 when the grasping portion 33A is inserted in the hole 13. Here, if the area S of the hole 13 is less than or equal to two thirds of the area D, as an example of one half of the area D shown in FIG. 12, the amount of freedom of the grasping portions 33A disappears and the insertion is difficult.

(Second Embodiment)

In the present invention, the constitution of a stent 102 differs from the first embodiment.

Figure 13:
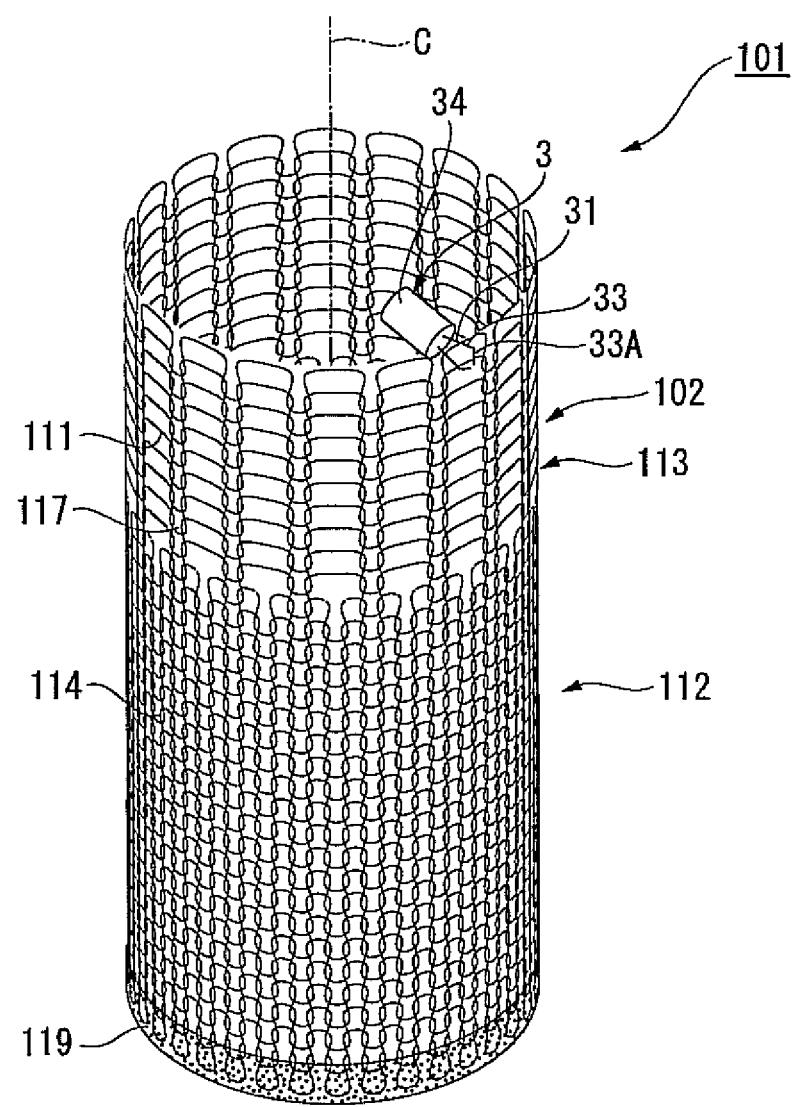
FIG. 13 shows the stent and the biological tissue being grasped by the clip.

As shown in FIG. 13, the stent 102 is formed to be a substantially circular by twisting a wire 111. The stent 102 has a stent main body 112 which is mainly used for enlarging the narrowed portion, and a locking portion 113 made of holes used for locking the stent 102 to the esophagus. A wire made of resins such as nylon, polypropylene, polylactate, polyglycolic acid, polycaprolactone, poly vinylidene fluoride, or polyester or the like is used for the wire for forming the locking portion 113. A threaded wire, which is made by a plurality of single wires threaded to form a wire, may be used instead of the single wire.

The stent main body 112 has a first mesh structure which is made by circular knitting (also called warp knitting) the single wire. That is, a first knitted loop 114 is formed by a wire 111, and the first knitted loops 114 are connected in the circumferential direction and twisted in a helix shape. Sizes of each of the first knitted loops 114 are substantially the same and a loop is formed by hooking another first knitted loop 114 which is adjacent in the direction along the center axis C. For this reason, each of the first knitted loops 114 is entwined one after the other to maintain a loop shape. The size of the inner diameter of the stent 102 is substantially constant when no outer force is applied. However, when a tensile force is applied to a direction directing to the center axis C, it is possible to shrink the outer diameter smaller by decreasing each of the first knitted loops 114.

Also, in each of the first knitted loops 114 which is circular knitted, an opening force, which is intended to enlarge the loop, is generated so that the cylindrical shape of the stent main body 12 is maintained.

The locking portion 113 has a second mesh structure which is made by circular knitting the wire 111 to form a substantially cylindrical shape. The outer diameter of the locking portion 113 is substantially equal to the outer diameter of the stent main body 112. The second mesh structure is made of second knitted loops 117 which are provided with half the number of knitted loops in the circumferential direction relative to the stent main body 112 for example so as to make the sizes of the knitted loops greater. Sizes of each of the first knitted loops 117 are substantially the same along the whole length so that the grasping portion 33A of the clip 3 can be inserted. The second loops 117 form a loop by hooking another second knitted loop 117 which is adjacent in the direction along the center axis C. For this reason, each of the second knitted loops 117 is entwined one after the other to maintain a loop shape.

The locking portion 113 is formed to be a portion provided with relatively rough knitted loops relative to the stent main body 112. In other words, the stent main body 112 is a portion with relatively fine knitted loops relative to the locking portion 113. By employing fine first knitted loops 114, the stent main body 112 is intended to assure the opening force and prevent jamming of the biological tissue. For this reason, the sizes of the first knitted loops 114 of the stent main body 112 may be such that the grasping portion 33A of the clip 3 cannot be inserted. The stent main body 112 and the locking portion 113 may be manufactured from a single wire 111, or the stent main body 112 and the locking portion 113 may be manufactured separately and connected by a connection thread (not shown).

Figure 14:
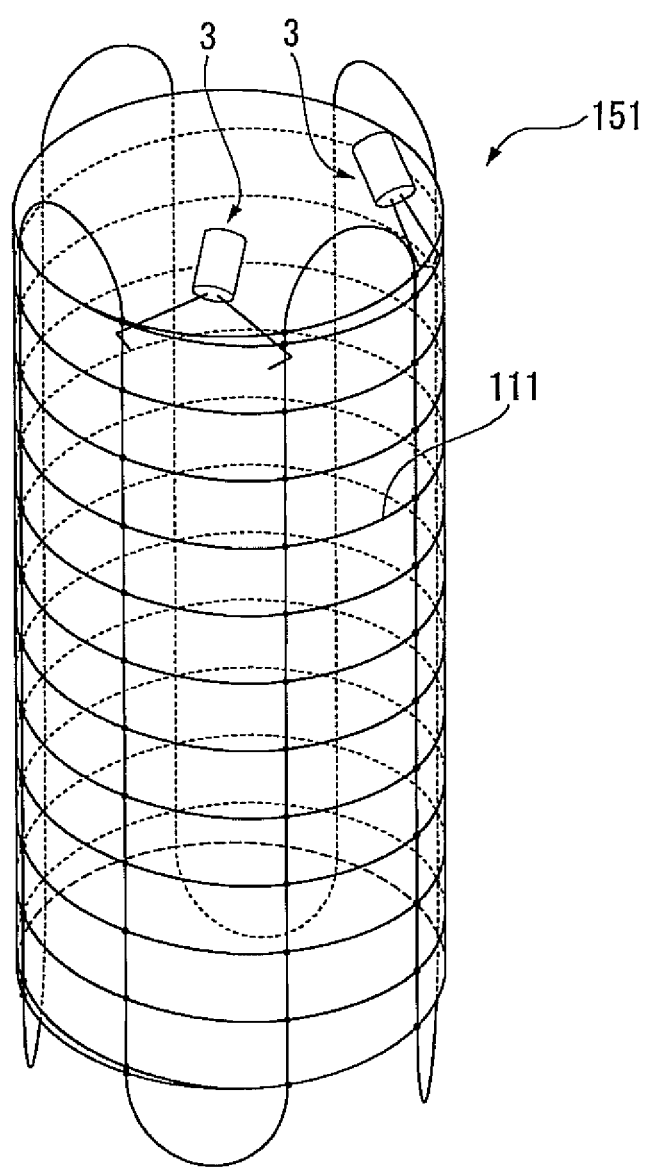
FIG. 14 shows an alternative example of the stent having a different stitching pattern.

Here, the end portion of the stent main body 112 along the center axis C is formed to be a connection portion 119 which is reinforced by a resin or an adhesive so as not to unplait the first knitted loops 114. The connection portion 119 may be formed by thermally sealing the wire 111. A similar connection portion may be formed at an end portion of the locking portion 113. Here, such a connection portion is not an essential element for the stent of the present embodiment. Also, the stent made of the wire may be a configuration as shown in FIG. 14 which is twisted in coil shape or may be other configurations forming holes. Here, a stent 115 shown in FIG. 14 has a constitution in which the wire 111 is twisted in a helix shape and partially connected in the axial line direction.

The clip 3 has a shape such that each of the arms 33 can be inserted one by one into the respective second knitted loop 117 of the locking portion 13. The maximum width L of the grasping portion 33A is smaller than the second knitted loop 117.

Figure 15:
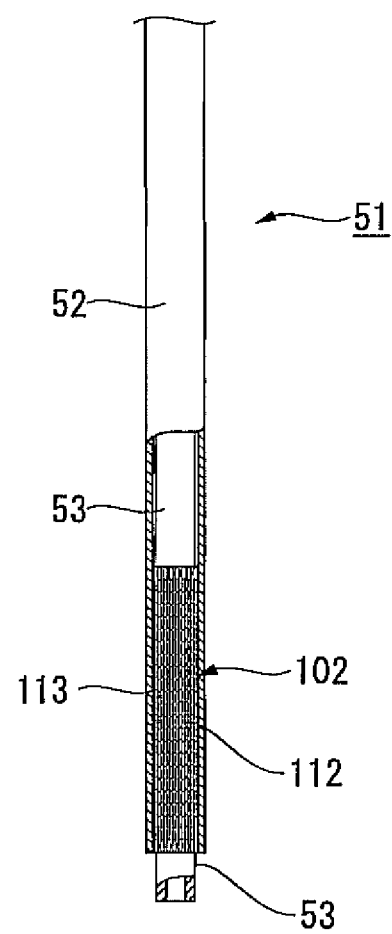
FIG. 15 is a partially cross-sectional view of the distal end portion of the stent delivery device.

A delivery device 51 of the stent 102 is shown in FIG. 15. The delivery device 51 has a double tubular constitution provided with an outer sheath 52 and an inner tube 53 having flexibility. Between both tubes 52, 53, the stent 102 is housed in a shrunken state. The stent 102 is disposed so that the locking portion 113 is disposed on the proximal end. The inner diameter of the inner tube 53 is formed to be able to insert an insertion portion of an endoscope therein.

Hereinbelow, an operation for placing a stent system 101 in accordance with the present embodiment shall be described.

Figure 16:
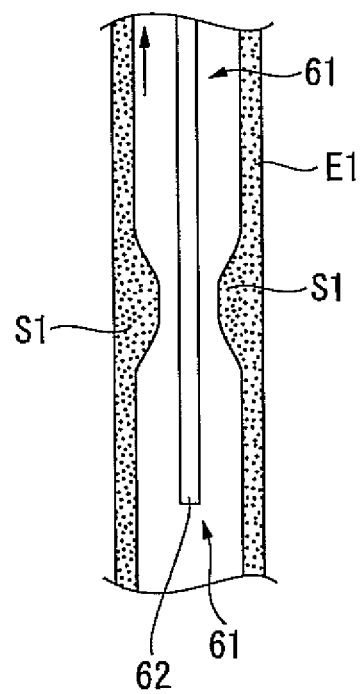
FIG. 16 shows a procedure which places the stent system, in which an endoscope is introduced to the vicinity of the narrowed portion.

As shown in FIG. 16, an insertion portion 62 of an endoscope 61 is inserted beyond a narrowed portion S1 of an esophagus E1. The position of the narrowed portion S1 is confirmed in advance by an observation device of the endoscope 61.

Figure 17:
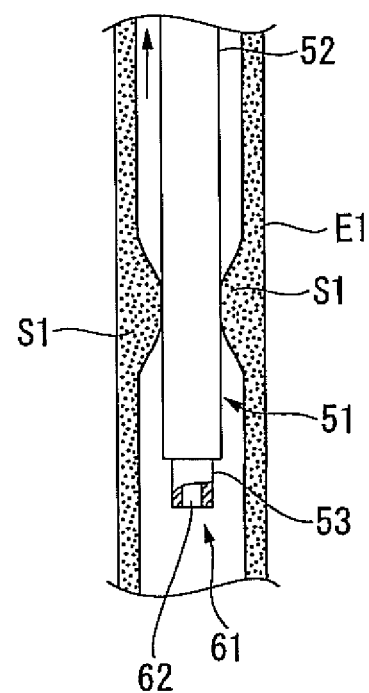
FIG. 17 shows a delivery device being introduced with the endoscope used as a guide.

Next, as shown in FIG. 17, the delivery device 51 placed in advance on the outer side of the insertion portion 62 of the endoscope 61 is extended with the endoscope 61 as a guide to a position beyond the narrowed portion S1.

Figure 18:
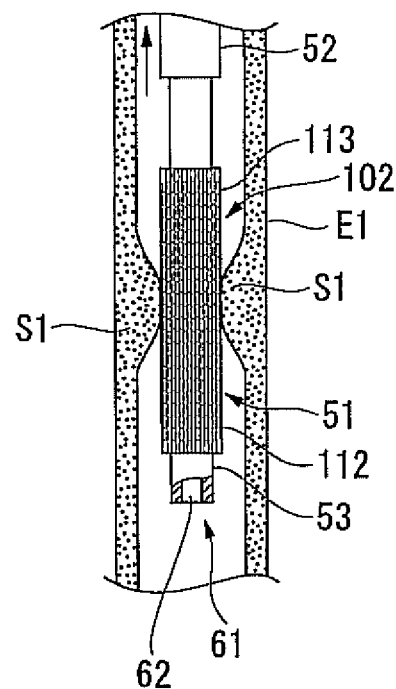
FIG. 18 shows a stent is exposed by retracting an outer sheath of the delivery device.
Figure 19:
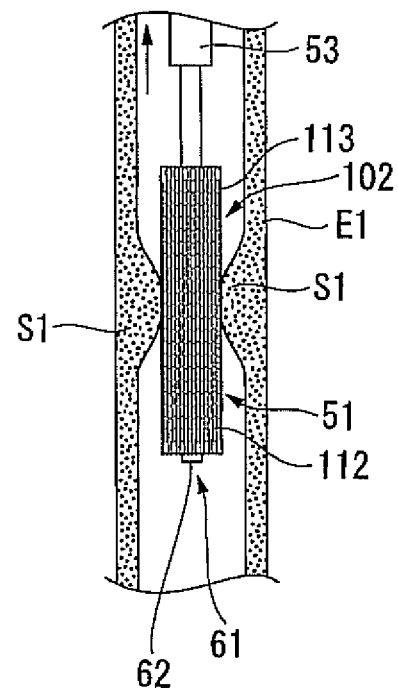
FIG. 19 shows the endoscope and the stent being left in place by retracting the inner tube.

The stent 102, which is shrunken as shown in FIG. 18, is exposed after retracting the outer sheath 52. Furthermore, when the inner tube 53 is retracted, the stent 102 remains in the narrowed portion S1 as shown in FIG. 19. After confirming the position of the stent 102 by the endoscope 61, the endoscope 61 is retracted from the stent 102.

When enlarging the stent 102, balloon or the like (not shown) inserted in an operation channel of the endoscope 61 is used.

Figure 20:
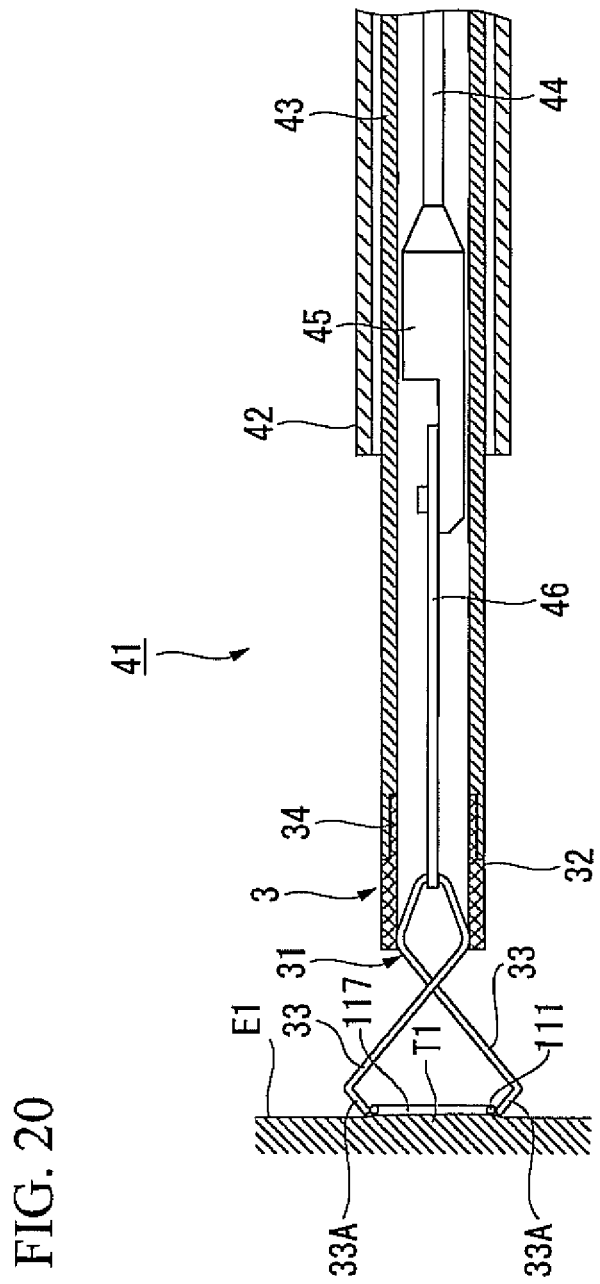
FIG. 20 shows an operation that drives a clip by the treatment tool which is inserted in the endoscope.

The clip 3 is driven so as to grasp the second knitted loop 117 of the locking portion 113 by inserting the instrument tool 41 shown in FIG. 6 in the operation channel of the endoscope 61. As shown in FIG. 20, the pusher sheath 43 is pushed out from the outer sheath 42 and the clip 3 is exposed. Since the outer sheath 42 which is biasing the distal ends of the clip 3 to close disappears, the pair of arms 33 of the clip 3 opens by its own elastic force. Each of the pair of arms 33 are inserted in the knitted loop 117 one by one, and the operation wire 44 is dragged by an operation at the side of the proximal end after positioning so that the wire 111 is positioned between each of the grasping portions 33A. The hook 46 is retracted and the ring portion 32 of the clip 3 is dragged into the pressing tube 34. When the hook 46 closes, the biological tissue T1 of the esophagus E1 is grasped with the state in which the wire 111 is positioned between the pair of arms 33. At this moment, the arm 22 deforms in accordance with the shape of the biological tissue T1 with which the wire is grasped or the disposition of the arms 33 so as to close the arms sufficiently.

Figure 21:
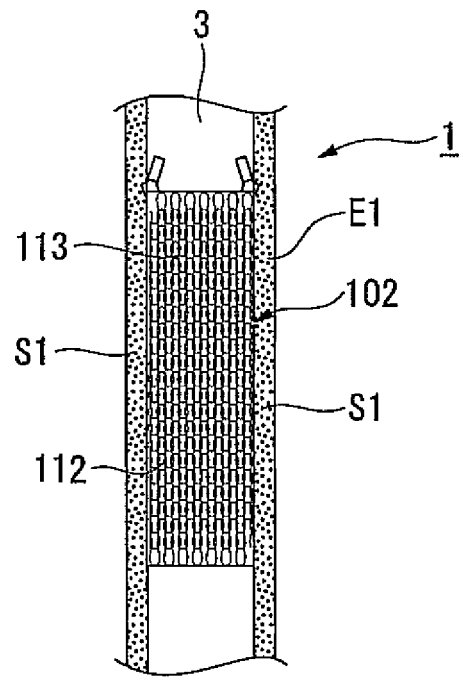
FIG. 21 shows the stent being opened and fixed by the clip.

When the operation wire 44 is dragged further, as shown in FIG. 2, a claw of the hook 46 is extended in line and departs from the clip 3. When the pusher sheath 43 is retracted, the pressing tube 34 separates from the pusher sheath 43 and the clip 3 is fixed in the esophagus E1. As shown in FIG. 21, the narrowed portion S1 of the esophagus E1 is enlarged by the stent system 101, a path for food or the like is ensured.

Figure 22:
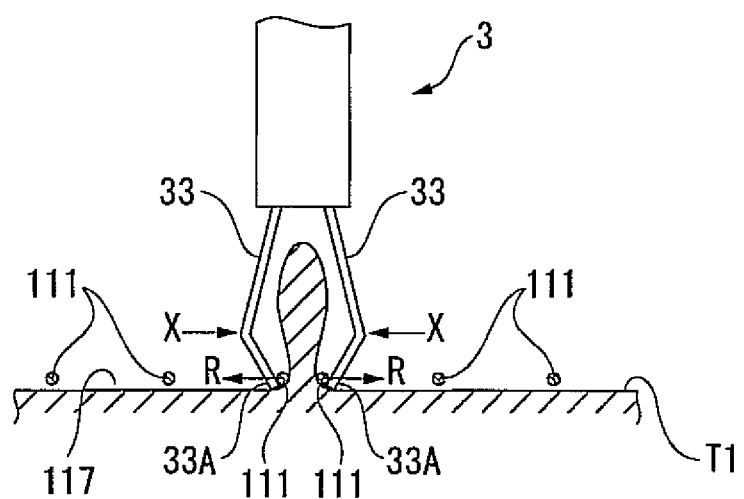
FIG. 22 shows the biological tissue being grasped by the grasping portion and a second stitching pattern being deformed.
Figure 23:
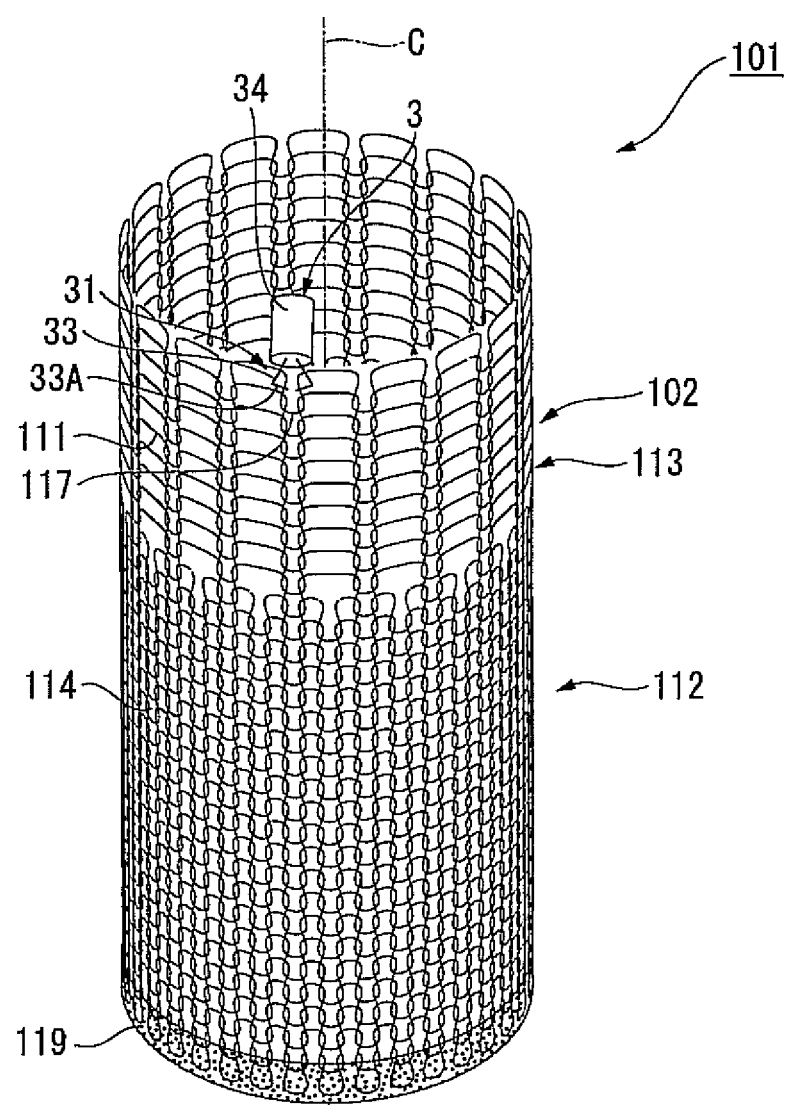
FIG. 23 shows another example of the clip grasping.

Here, as shown in FIG. 23, it is preferable that the clip 3 is installed so that the clip 3 grasps the biological tissue T1 and the wire 111 from the center axis C. As shown in FIG. 22, the grasping force X of the clip 3 has the relationship of X>R between the drag R of the wire 11 which is grasped. Therefore, the pair of grasping portion 33A presses the wire 111 to move closer and grasps the biological tissue T1 while deforming the second knitted loop 117. As a result, the wire 111 and the biological tissue T1 are reliably grasped by the clip 3. When the clip 3 is installed in this direction, the second knitted loop 117 does not collapse in the circumferential direction, it is possible to prevent the diameter of the stent 2 from being decreased. In FIG. 9 and FIG. 10, the clip 3 can grasp and fix the stent 2 with the biological tissue at arbitral position and orientation.

In FIG. 13, each of the arms 33 is inserted into each of the second knitted loops 117 which are adjacent along the center axis C. Each of the arms 33 may be inserted into both ends of the three of the second knitted loops which are adjacent in the center axis C direction. In this way, the biological tissue T1 is grasped in a state in which a second knitted loop 117 is positioned between the pair of arms 33. In this case, when the clip 3 is open, the distance between the grasping portions 33A of the pair of arms 33 is greater than the size of the second knitted loop 117, and is set smaller than three times the size of the second knitted loop 117. When the clip 3 is close, it is preferable that the distance between the pair of arms 33 is smaller than the size of the second knitted loop 117. It is possible to fix the stent 102 reliably since it is possible to lock the stent 102 with the second knitted loop 117 being collapsed, which is sandwiched between the pair of arms 33.

Here, the clip 3 may grasp the biological tissue T1 and the wire 111 from a direction perpendicular to the center axis C direction as shown in FIG. 13, which is a direction perpendicular to the direction shown in FIG. 23. From this direction, it is possible to grasp the wire 111 and the biological tissue T1 with the clip 3 by the second knitted loop 117 being deformed.

When the stent 102 is removed, the wire 111 may be dragged and the first knitted loop 114 and the second knitted loop 117 may be loosened. In this case, a grasping forceps (not shown) is inserted into the endoscope and the end portion of the wire 111 is dragged while removing adhesives or the like from the connection portion 119 with the grasping forceps. Then the first knitted loop 114 and the second knitted loop 117 of the stent 102, which is made by circular knitting, are loosened in order. When the stent 102 is made of a wire 111, it is possible to break down and recover the whole stent 102 by dragging the end portion of a wire 111. When the stent main body 112 and the locking portion 113 is connected by the connection thread, die wire 111 is dragged and loosened from each of the end portions and the leftover connection thread is recovered.

A conventional stent was made of metal or bard plastic and it was difficult to grasp it with the biological tissue with the clip. In the present embodiment, the second knitted loop 117, which can be deformed by the grasping force of the clip 3, is provided. Therefore, it is possible to grasp the stent 102 with the biological tissue T1 by the clip 3. Accordingly, it is possible to reliably place the stent 102 at desired position in the hollow organs such as the esophagus E1.

Since the second knitted loop 117 of the locking portion 113 is made greater than the first knitted loop 114 of the stent main body 112, it is possible to easily insert the clip 3 and it is possible to easily grasp the biological tissue T1 through the second knitted loop 117. In contrast, the first knitted loop 114, in which the clip 3 is not inserted, can reliably be a size necessary to enlarge the narrowed portion S1.

(Third Embodiment)

Figure 24:
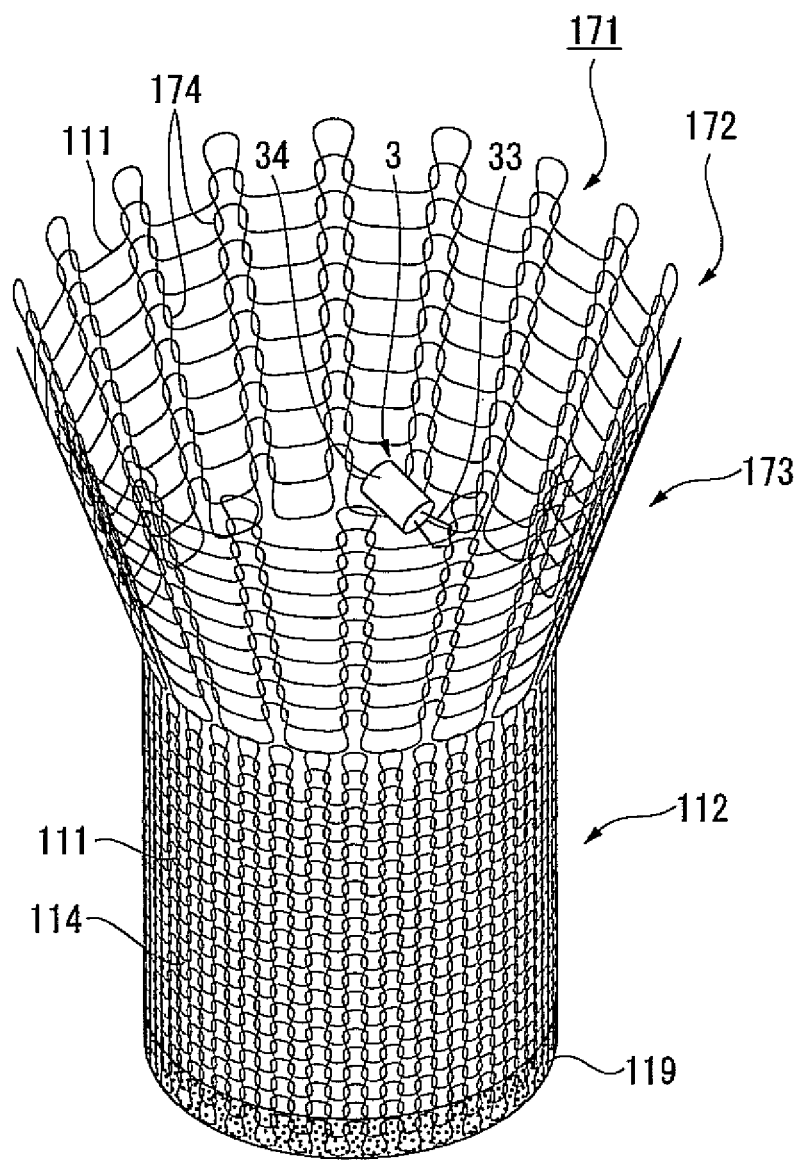
FIG. 24 shows an overview of the stent having a locking portion which opens in tapered shape.

As shown in FIG. 24, the stent system 171 has a stent 172 and at least a clip 3. The stent 172 has the stent main body 112 and a locking portion 173 which increases its diameter from the stent main body 112 in a tapered shape.

The locking portion 173 has a second mesh structure which is made by circular knitting the wire 111 to form a substantially cylindrical shape provided with holes. The second mesh structure has second knitted loops 174 (hereinbelow simply called a second knitted loop), which are holes greater than the stent main body 112, and formed so as to gradually open from the stent main body 112 to an end portion. The number of the knitted loops in the circumferential direction may be the same both at the stent main body 112 and at the end portion so that the size of the knitted loops increases gradually. On the other hand, the sizes of the knitted loops may be substantially the same and the sizes of the knitted loops may be gradually increased toward the end portion of the knitted loops in the circumferential direction. The wire 111 of the locking portion 173 may be the same as the stent main body 112 or the stent main body 112 with a different structure may be connected. The locking portion 173 may be connected to the stent main body 112 by the connection thread or may be integrally knitted with the stent main body 112 by the same wire 111 as the stent main body 112.

When the procedure is performed, the stent system 171 is inserted in the esophagus E1 from the side of the stent main body 112. The arms 33 of the clip 3 are inserted in the second knitted loops 174 of the locking portion 73 one by one and the clip 3 is fixed to the narrowed portion S1 of the esophagus E1 by grasping the biological tissue T1. The clip 3 may be disposed so that the arms 33 thereof are inserted one by one in the adjacent two second knitted loops 174 in the center axis C direction or in the circumferential direction. The clip 3 may also be disposed so that the arms 33 thereof are inserted one by one in knitted loops located at both ends of the adjacent three second knitted loops 174. In either case, when the clip 3 is closed, a wire 11 placed between the pair of arms 33 deforms and reliably closes the pair of arms 33.

This stent 172 obtains the same effects as the stents described above. Since it is possible to form the second knitted loops 174 at the locking portion 173 large, it is even easier to fix by the clip 3. Also, the enlarged locking portion 173 is easy to adhere to the esophagus and so it is easy to fix with the clip 3.

Here, alternative examples of the present invention shall be described.

Figure 25:
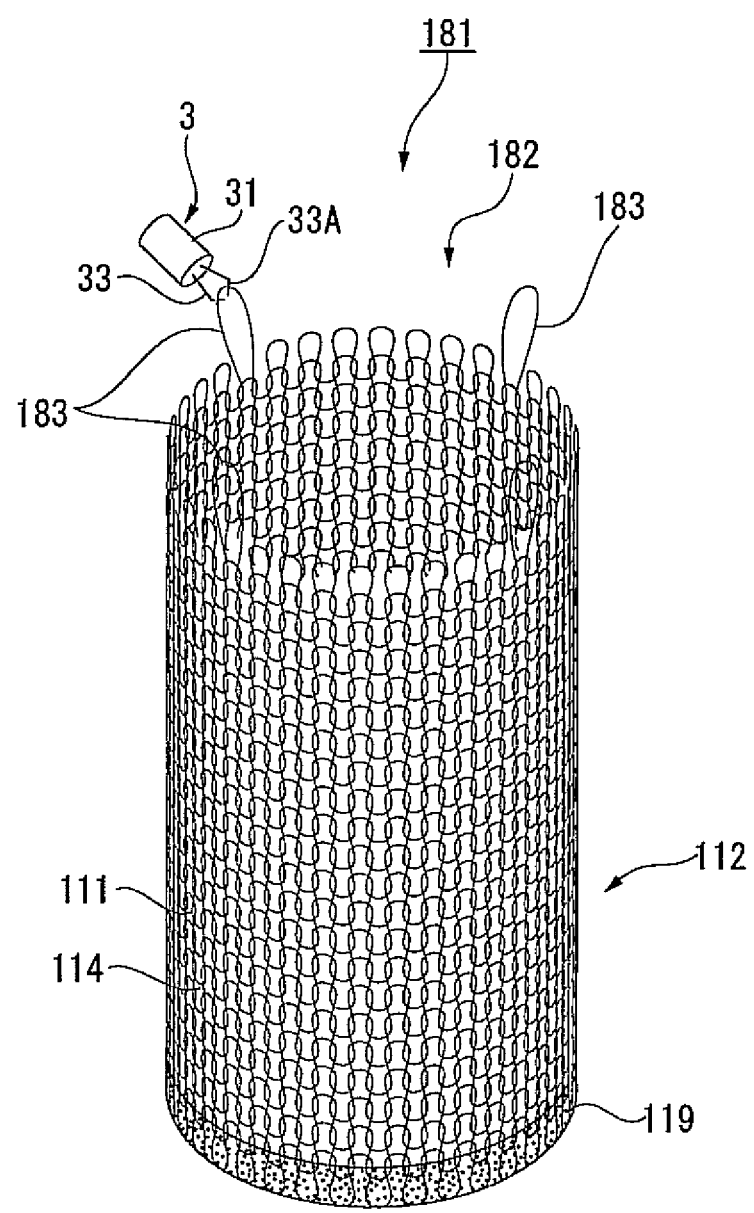
FIG. 25 shows an overview of the stent having the locking portion formed by a large stitching pattern.

A stent system 181 shown in FIG. 25 has a stent 182 and at least a clip 3. The stent 182 has the stent main body 112 and second knitted loops 183 provided at the end portion of the stent main body 112 as locking portions. The second knitted portion 183 is made of a loop of the wire 111, is greater than first knitted portions 114 of the stent main body 112, and is provided with a plurality of intervals in the circumferential direction. When the stent 182 is fixed, both of the wire 111 of the second knitted loops 183 and the biological tissue T1 are grasped by the clip 3. The wire 111 forming the second knitted loops 183 deforms and reliably closes the arms 33 of the clip 3. By proving the locking portions partially, it is possible to form the outer shape of the stent 182 so as to be small. By forming the knitted loops 183 functioning as locking portions large in size, it is easy to fix with the clip 3. At this moment, deformation of the locking portion is small and deformation of the stent in the axis direction or in the radial direction is restrained at a minimum level.

Figure 26:
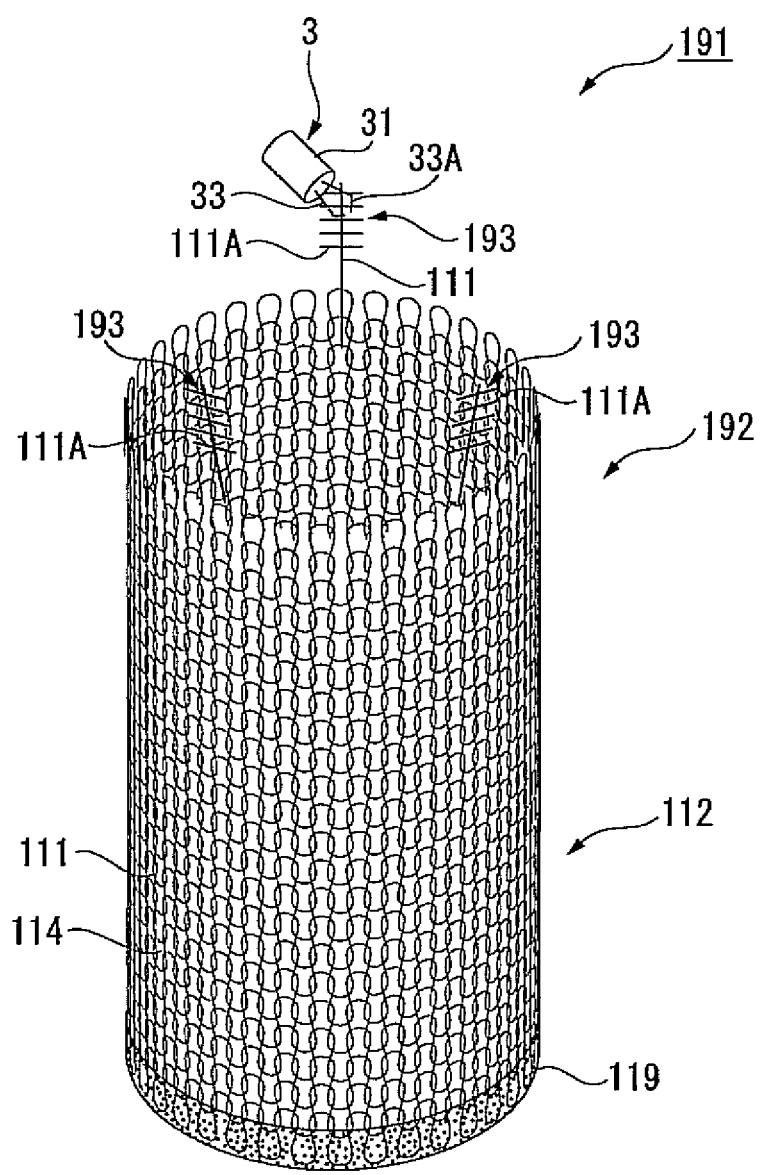
FIG. 26 shows an overview of the stent having a constitution in that the locking portion extends branch pipes to the right and the left of a wire.

A stent system 191 shown in FIG. 26 has a stent 192 and at least a clip 3. The stent 192 has the stent main body 112 and a locking portion 193 provided with intervals at the end portion of the stent main body 112. In each of the locking portions 193, branch tubes 111A are extended left and right from a wire 111 which is extending in radial direction from the stent main body 112. For example, each of the pair of branch tubes 111A are provided at predetermined intervals along the length direction of the wire 111. When fixing with the clip 3, the biological tissue T1 is grasped so as to sandwich the locking portion 193 with the pair of arms 33. The wire 111 is made of a rigid body and so it does not deform in the axis direction or in the radial direction. However, the branch tubes 111A deform and the arms 33 of the clip 3 reliably close and the clip 3 is fixed.

Figure 27:
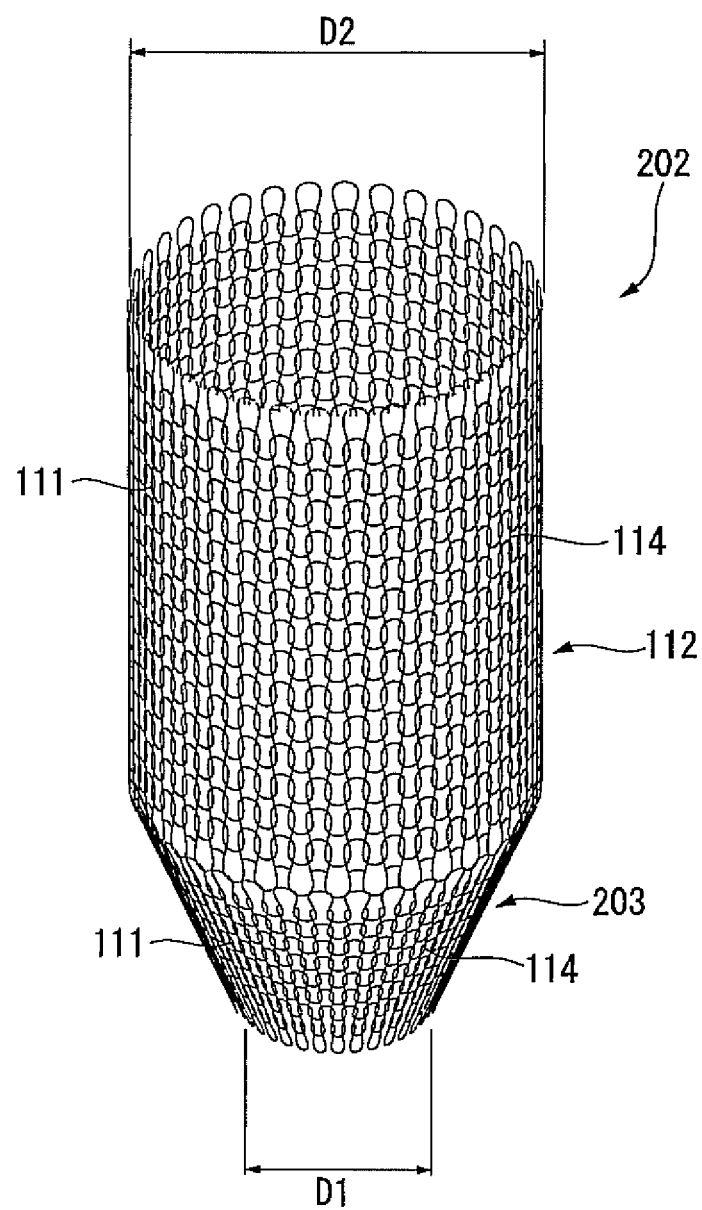
FIG. 27 shows an overview of the stent having a portion with decreased diameter at a distal end of the stent main body.
Figure 28:
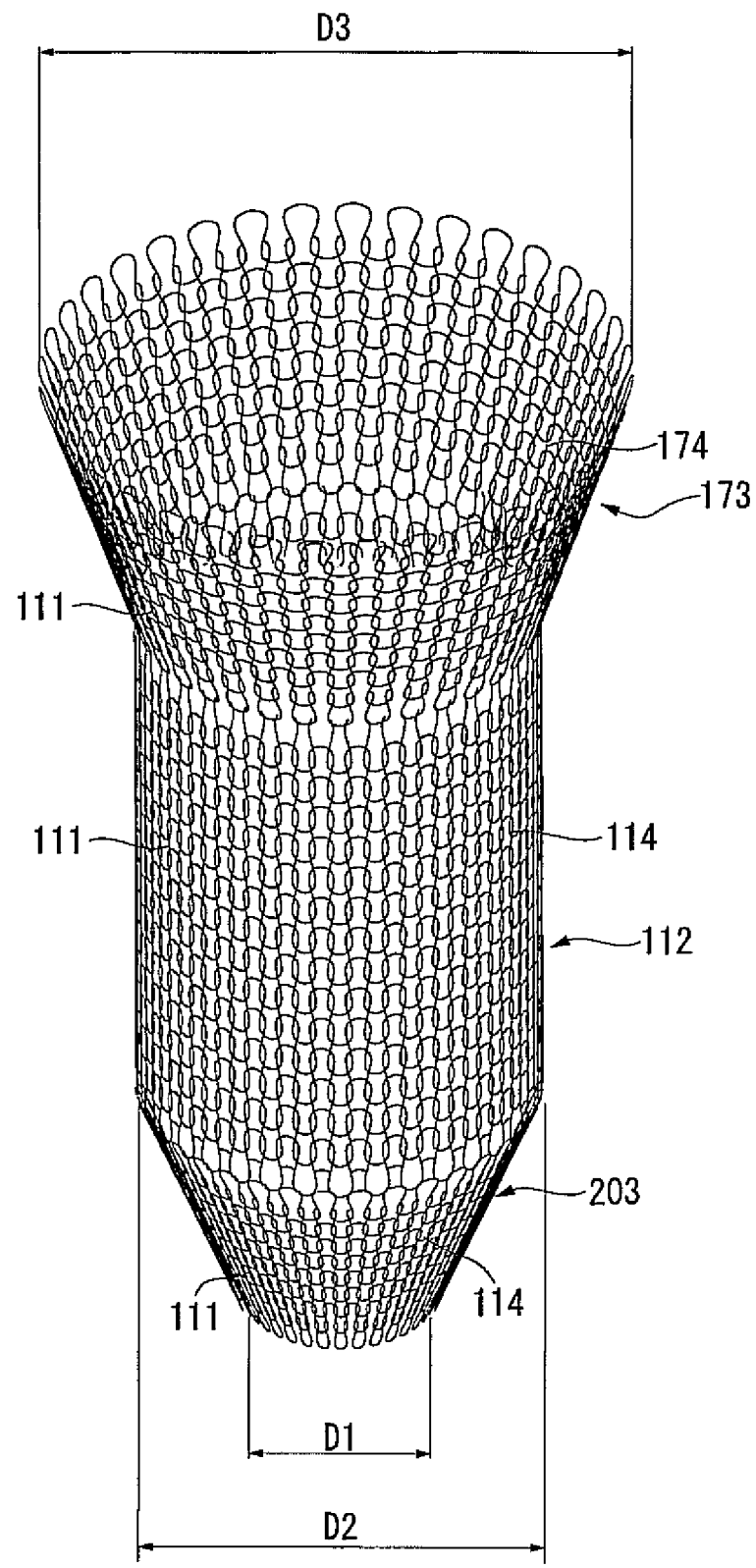
FIG. 28 shows an overview of the stent provided with the locking portion shown in FIG. 24 to the stent main body shown in FIG. 27.

A stent 202 shown in FIG. 27 has a third mesh structure in which one of the end portions of the stent main body 112 decreases in diameter closer to the end portion. A diameter decreased portion 203 provided with the third mesh structure is decreasd in diameter by sewing the end portion of the stent main body 112 for example. A diameter D1 at the distal end of the diameter decreased portion 203 is smaller than a diameter D2 of the end portion of the stent main body 112. In this stent 202, insertionability further improves. When any of the above described locking portions are additionally used, it is possible to reliably fix the stent in a desired position. For example as shown in FIG. 28, the locking portion 173, which increases its diameter, may be used. The maximum diameter D3 of the locking portion 173 is greater than the diameter D2 of the stent main body 112 and the minimum diameter D1 of the diameter decreased portion 203.

Here, the present invention is not limited to the above described embodiments but can be widely applied.

For example, the stent may be used not only in an esophagus but also for enlarging the narrowed portion of a bile duct or the like.

The clip may have an aspect of being used by being inserted in a knitted loop and of grasping a biological tissue. Three or more of the arms may be provided. A treatment tool for driving the clip is not limited to structures disclosed in the embodiments. A stent delivery device is not limited to structures disclosed in the embodiments either.

The locking portion 173 of the third embodiment is constituted so that the diameter thereof increases continuously but the diameter thereof may be changed discontinuously. Both the stent main body 112 and the locking portion 173 may have discontinuous diameters.

Figure 29:
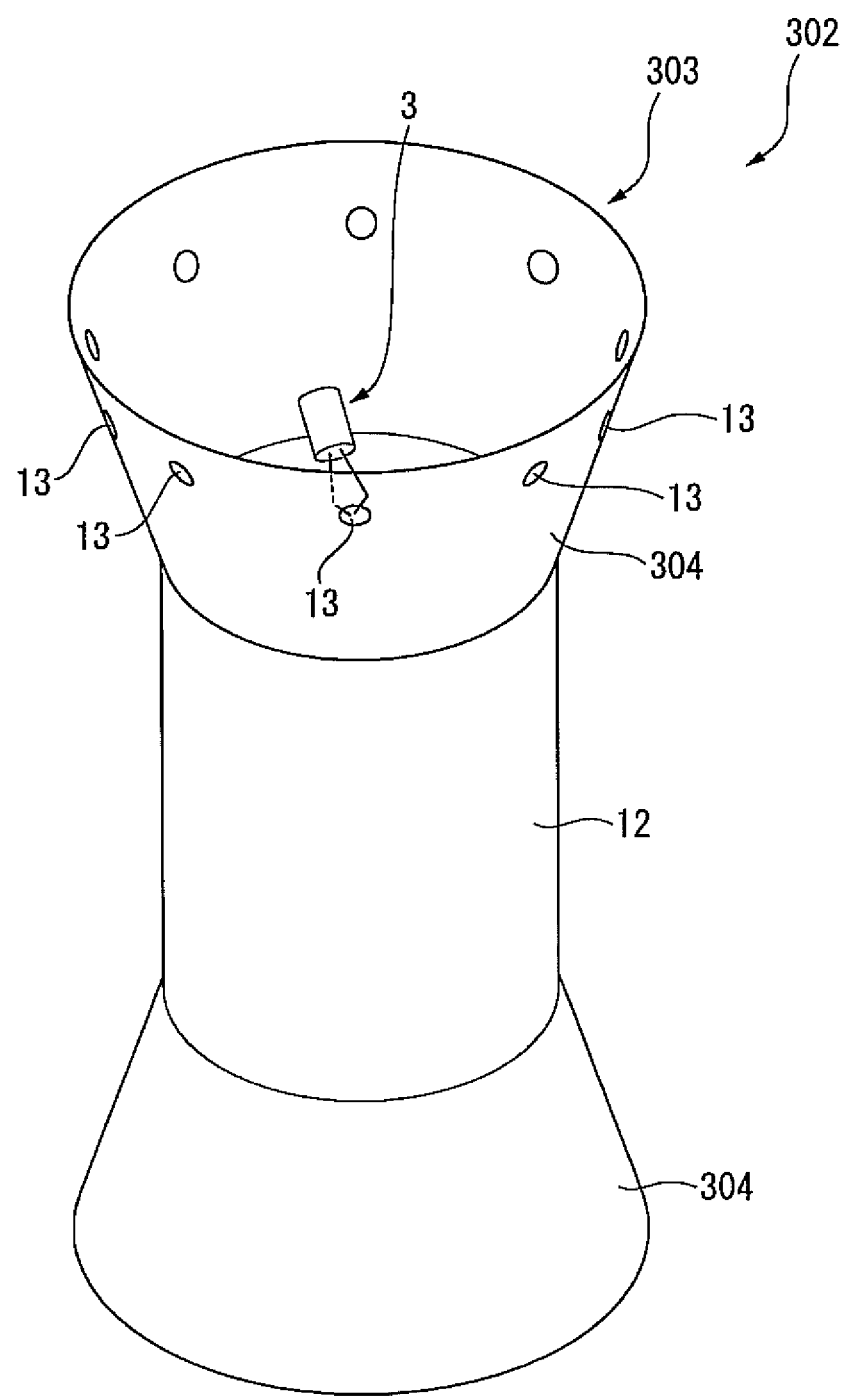
FIG. 29 shows an alternative example of the stent.

As a stent 302 shown in FIG. 29, both end portions 304 in the length direction of the stent main body 12, in which a film is formed in cylindrical shape, are formed to be tapered shapes in which diameters thereof increase and holes 13 may be formed thereon.

In accordance with the stent system of the first aspect of the present invention, it is possible to fix the stent directly to the hollow organ by introducing and disposing the stent to an object portion in the hollow organ and inserting at least one grasping portion located at the distal end of the arm of the anchor in the hole of the stent, and grasping the stent together with the biological tissue of the hollow organ.

In accordance with the stent system of the second aspect of the present invention, it is possible to fix the stent by easily passing the grasping portion of the anchor through the hole.

In accordance with the present invention, it is possible to easily pass the grasping portion of the anchor through the hole when fixing the stent to the hollow organ by the anchor.

Also, since the stent portion which is grasped is deformed, it is possible to reliably grasp the stent and the living tissue in the hollow organ by sufficiently closing the arm of the anchor.

It is possible to prevent the dislocation of the stent by the anchor reliably grasping the stent and the living tissue in the hollow organ.

What is claimed is:

1. A stent system comprising:
   a stent having a cylindrical shape and configured to be inserted in a hollow organ; and
   an anchor being separate from the stent, the anchor comprising a first arm and a second arm,
wherein:
   the stent is provided with holes,
   the first arm and the second arm are configured to be inserted in each hole respectively,
   in a state where the first arm and the second arm are inserted in the respective hole, the stent is capable of being deformed such that a part of an edge part of the holes which is positioned between the first arm and the second arm, approaches each other by closing the first arm and the second arm, and
   the anchor is configured to be capable of grasping both a portion of the hollow organ and the stent while deforming a part of the stent to fix the stent to the hollow organ.

2. The stent system according to claim 1,
   wherein the anchor further comprises grasping portions located at distal ends of the first arm and the second arm, respectively,
   wherein the grasping portions are configured to be inserted into the holes of the stent, and
   wherein each of the holes in which the grasping portions are inserted has an area which is two-thirds or more of an area of a circle having a diameter, the diameter being the same as a maximum width of the corresponding grasping portion.

3. The stent system according to claim 1, wherein distal ends of the first and second arms are bent toward each other.

4. The stent system according to claim 3, wherein the distal ends of the first and second arms are configured to grasp the portion of the hollow organ so as to cause the portion of the hollow organ to be interposed between the distal ends.

* * * * *